United States Patent [19]

Karol

[11] Patent Number: 5,597,785

[45] Date of Patent: *Jan. 28, 1997

[54] SUCCINIMIDE DERIVATIVES OF 2,5-DIMERCAPTO-1,3,4-THIADIAZOLE

[75] Inventor: Thomas J. Karol, Norwalk, Conn.

[73] Assignee: R. T. Vanderbilt Company, Inc., Norwalk, Conn.

[*] Notice: The portion of the term of this patent subsequent to Apr. 22, 2011, has been disclaimed.

[21] Appl. No.: 494,828

[22] Filed: Jun. 26, 1995

Related U.S. Application Data

[63] Continuation-in-part of Ser. No. 189,260, Jan. 31, 1994, abandoned, which is a continuation-in-part of Ser. No. 770,000, Oct. 2, 1991, abandoned.

[51] Int. Cl.$^6$ .............. C10M 141/06; C10M 141/08; C07D 285/14
[52] U.S. Cl. ................ 508/274; 525/349; 525/382; 548/142
[58] Field of Search .............. 252/47.5; 525/382; 525/349; 548/142; 508/274

[56] References Cited

U.S. PATENT DOCUMENTS

| | | | |
|---|---|---|---|
| 3,287,271 | 11/1966 | Stuart et al. | 252/49.9 |
| 3,567,638 | 3/1971 | Braid | 252/46.7 |
| 4,140,643 | 2/1979 | Davis | 252/47.5 |
| 4,482,464 | 11/1984 | Karol et al. | 252/51.5 |
| 4,618,438 | 10/1986 | Toukan et al. | 252/47.5 |
| 4,902,804 | 2/1990 | King et al. | 548/130 |
| 5,055,584 | 10/1991 | Karol | 252/47.5 |
| 5,102,568 | 4/1992 | King et al. | 252/47.5 |
| 5,110,491 | 5/1992 | Derosa et al. | 252/47.5 |

FOREIGN PATENT DOCUMENTS

| | | | |
|---|---|---|---|
| 0218816 | 4/1987 | European Pat. Off. | |
| 1462287 | 1/1977 | United Kingdom | C10M 1/38 |

*Primary Examiner*—Margaret Medley
*Attorney, Agent, or Firm*—Rasma B. Balodis

[57] ABSTRACT

Disclosed the novel compounds prepared by reacting 2,5-dimercapto-1,3,4,-thiadiazole with maleic anhydride and N-polyethylene amine-substituted succinimide. The compounds are dispersants or detergents, antiwear agents and antioxidants when incorporated into lubricating compositions.

4 Claims, No Drawings

1

SUCCINIMIDE DERIVATIVES OF 2,5-DIMERCAPTO-1,3,4-THIADIAZOLE

This application is a Continuation-In-Part of application Ser. No. 08/189,260 filed on Jan. 31,1994, now abandoned which is a Continuation-In-Part of application Ser. No. 07/770,000 filed on Oct. 2, 1991, now abandoned.

BACKGROUND OF THE INVENTION

The present invention concerns novel succinimide derivatives of 2,5-dimercapto-1,3,4-thiadiazoles and their use as multifunctional additives for lubricating compositions.

Lubricating compositions ordinarily are formulated with various additives to enhance their performance. A problem sometimes encountered is that a particular additive has low solubility in oil or a combination of additives decreases the solubility of other additives in the lubricating composition resulting in undesirable haze or sediment formation. Therefore, it is desirable to use lubricating additives that can perform different functions.

The use of multifunctional lubricating additives containing the 2,5-dimercapto-1,3,4-thiadiazole group is known. 2,5-Dimercapto-1,3,4-thiadiazole is commonly called DMTD. Many DMTD derivatives have poor oil solubility and are incorporated into lubricating compositions with the aid of dispersants. However, dispersants employed in crankcase lubricating oils can degrade the elastomeric seals used in internal combustion engines. The dispersants can decrease the flexibility of the seals and increase their hardness causing crack formation.

Prior art dispersants include various nitrogen-bridged dispersants, including alkenylsuccinimide type. British Pat. No. 1,462,287 describes, among others, various succinimide dispersants which may be used to disperse dimercaptothiadiazoles having copper inhibiting activity. Specifically, a dispersant and 2,5-dimercapto-1,3,4-thiadiazole is interacted in amounts substantially greater than the stoichiometric amount necessary for salt formation. The precise chemical nature of the obtained homogeneous blends is not given. This intermediate blend can be reacted with a carboxylic acid to form a product of uncertain structure as described in U.S. Pat. No. 4,140,643.

Surprisingly, it has been discovered that certain amine dispersant derivatives of 2-(2-mercapto-1,3,4-thiadiazole-5-thio) succinic anhydride retain dispersant properties as well as display antiwear and antioxidant properties. The novel additives are compatible with elastomeric seals used in engines.

SUMMARY OF THE INVENTION

In accordance with the invention, there are provided novel 1,3,4-thiadiazole compounds characterized by the structural formula

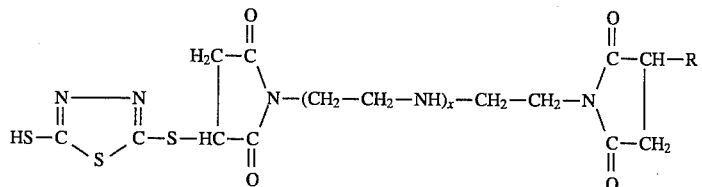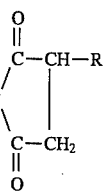

wherein x=0 to 4, and R represents an alkenyl radical having from 8 to 400 carbon atoms.

Another aspect of the invention concerns improved oil-based lubricating compositions comprising a major amount of base oil and an effective amount to impart antiwear and antioxidant properties to said compositions, of a 1,3,4-thiadiazole characterized by formula I.

A further aspect of the invention concerns a method for protection of internal combustion gasoline type engine parts from wear by applying improved lubricating oil compositions, the improvement of which consists of adding to the compositions an effective amount of a 1,3,4-thiadiazole characterized by the structural formula I.

DESCRIPTION OF SPECIFIC EMBODIMENTS

The novel compounds of the invention may be prepared by reacting DMTD with maleic anhydride to yield the intermediate of the structural formula

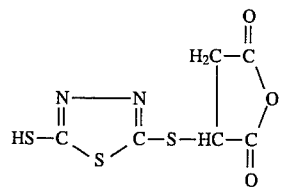

or its isomer. The intermediate is then reacted with N-polyethylene polyamine substituted succinimide to yield compounds of formula I.

The N-polyethylene polyamine-substituted succinimide reactants having dispersant properties are available commercially. A general preparation method is disclosed in U.S. Pat. No. 3,287,271. The dispersants are derived from alkenylsuccinic anhydride wherein the alkenyl group contains 8 to 400 carbon atoms and preferably from about 50 to 200 carbon atoms.

Particularly preferred are alkenyl groups derived from polyisobutene. The alkenyl radical is readily obtained by polymerizing olefins having 2 to 5 carbons, such as ethylene, propylene, isobutylene, pentene and similar alkenes.

The amine radical is derived from a polyamine of the formula $H_2N(CH_2-CH_2-NH)_x-CH_2-CH_2-NH_2$. Preferred compounds are wherein x is an integer from 0 to 4.

The thiadiazole derivatives of the invention are useful as additives for industrial lubricating compositions and engine oil formulations, as for example two cycle oils used in internal combustion engines. Particularly preferred application is in lubricating formulations intended for automotive gasoline type engines.

The thiadiazole compounds possess multifunctional properties. They perform antiwear and oxidation inhibiting functions and are effective dispersants in lubricants and in engine oils. The dispersant property of the compounds facilitates their incorporation into the oil compositions and contribute to the overall stability and performance of the oil composition.

(I)

The lubricating compositions contemplated herein include lubricating oils, engine oils and lubricating greases containing a major amount of base oil. The base oil may be selected from naphthenic, aromatic, paraffinic, mineral, vegetable and synthetic oils. The synthetic oils may be selected from, among others, alkylene polymers, polysiloxanes and carboxylic acid esters.

The amount of the thiadiazole additive required to be effective for imparting antiwear and antioxidant characteristics to lubricating compositions may range from about 0.01 to 15.0 percent of the additive based on the lubricating composition.

The lubricating compositions may contain the necessary ingredients to formulate the compositions, as for example emulsifiers, other dispersants and viscosity improvers. Greases may be prepared by adding thickeners, as for example, salts and complexes of fatty acids, polyurea compounds, clays and quaternary ammonium bentonite complexes. Depending on the intended use of the lubricant, other functional additives may be added to enhance a particular property of the lubricant. The lubricating compositions may further contain extreme pressure agents, metal passivators, rust inhibitors, dispersants and other known antioxidants and antiwear agents.

The following examples are given for the purpose of further illustrating the invention. All percentages and parts are based on weight unless otherwise indicated.

EXAMPLE 1

A reactor was charged with DMTD, 312.84 g, and dimethyl ketone as solvent, 722 g. Maleic anhydride, 196 g, was dissolved in dimethyl ketone solvent, 300 g, and added to the reaction with cooling. The reaction was stirred for 30 min. and warmed to 50° C. The intermediate product, a thiadiazolyl succinic anhydride in the form of white powder, was recovered from the solvent by filtering.

The air-dried thiadiazolyl succinic anhydride interemediate, 38 g, and 516.5 g of 50% N-triethylenetetraamine polyisobutenylmonosuccinimide, mol. wt. 1522, in oil diluent (TC-9596A manufactured by Texaco) were reacted at 135°–140° C. for 2 hours and filtered to afford the final product in oil diluent. The product is characterized by the formula I wherein x is 2 and R is polyisobutenyl.

EXAMPLE 2

Modified Falex Wear Test

A laboratory test was conducted by using the original Falex machine to simulate the valve train wear of an automobile engine. The V-blocks and pin were washed in mineral spirits with an ultrasonic cleaner, rinsed with acetone, air-dried and weighed. The test sample (60 g) was placed into the oil cup. The motor was switched on and the loading arm was placed on the ratchet wheel. Upon reaching the reference load of 227 kg, the ratchet wheel was disengaged and the load was maintained constant for 3.5 hours. Thereafter, the motor was switched off. The V-blocks and pin were washed, dried and weighed. The weight loss, a measure of wear, was recorded and compiled in Table I.

The test samples were prepared by incorporating the compounds of the invention in Motor Oil SAE 30, SF in the amount given in Table I. The oil was fully formulated with the exception of the antioxidant additive and contained 0.11 percent phosphorus. The results indicate that the present compounds afford good antiwear properties.

TABLE I

Modified Falex Wear Test

| Sample | Active Ingredient | Percent | Total Weight Loss, mg |
|---|---|---|---|
| 1 | None | — | 57.2 |
| 2 | Compound of Example 1 | 5.0 | 22.1 |

EXAMPLE 3

Thin Film Oxygen Uptake Test

The test was conducted essentially according to the method described by Chia-Soon et al, *J. Am. Soc. Lubricating Eng.*, 40, 2 75–83, 1984. The oxidation induction time of the lubricant was measured under conditions simulating the high temperature oxidation processes in automotive engines by a modified rotary bomb oxidation test method ASTM D-2272. The test was conducted with 1.5 gram samples of SAE 30, SF motor oil. The oil was fully formulated with the exception of the antioxidant additive. A compound of the invention was added to the oil in the amount indicated in Table II. The test was conducted at 160° C. and initial oxygen pressure of 620.6 kPa (90 psi). A "pass" oil has a high induction time, while a "fail" oil has a low time. The additive of the invention has good antioxidant properties as indicated by the data compiled in Table II.

TABLE II

Thin Film Oxygen Uptake Test

| Sample | Active Ingredient | Percent | Average Induction Time, min. |
|---|---|---|---|
| 3 | None | — | 108.0 |
| 4 | Compound of Example 1 | 5.0 | 162.5 |

The above embodiments have shown various aspects of the present invention. Other variations will be evident to those skilled in the art of such modifications are intended to be within the scope of the invention as defined by the appended claims.

What is claimed is:

1. A thiadiazole compound selected from the group of compounds having the structural formula

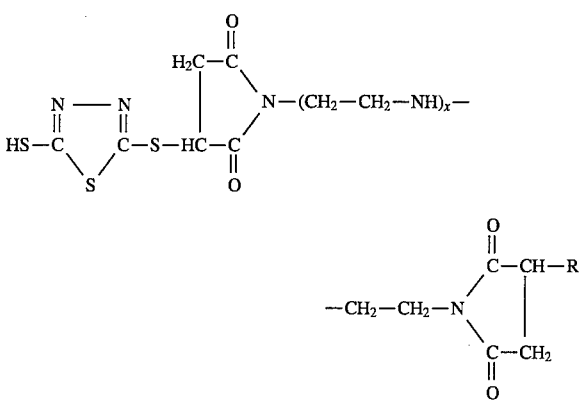

wherein x=0 to 4, and R represents an alkenyl radical having from 8 to 400 carbon atoms.

2. A compound according to claim 1 wherein the alkenyl radical is polyisobutene.

3. An automotive gasoline engine lubricating composition comprising a major portion of natural or synthetic oil of lubricating viscosity and a minor antiwear and oxidation inhibiting amount of a compound selected from the group consisting of compounds having the structural formula

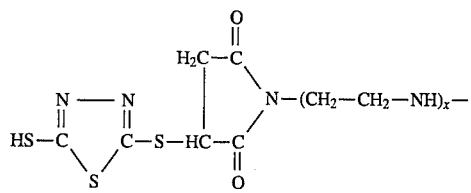

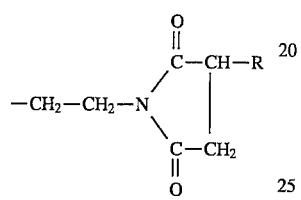

wherein x=0 to 4, and R represents an alkenyl radical having from 8 to 400 carbon atoms.

4. A method for protecting automotive gasoline engine parts from wear and deterioration which comprises contacting the surfaces with a lubricating composition comprising a major amount of base oil of lubricating viscosity, the improvement of which consists of adding to the oil a minor antiwear and oxidation inhibiting amount of an additive selected from the group of compounds having the structural formula

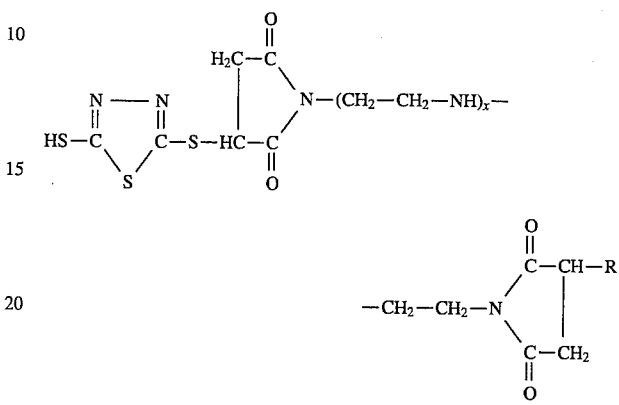

wherein x=0 to 4 and R represents an alkenyl radical having from 8 to 400 carbon atoms and dispering additive into the base oil.

* * * * *